US008847960B2

United States Patent
Elie et al.

(10) Patent No.: US 8,847,960 B2
(45) Date of Patent: Sep. 30, 2014

(54) METHOD AND SYSTEM FOR QUANTIFICATION OF TUMORAL VASCULARIZATION

(75) Inventors: Nicolas Elie, Ifs (FR); Nathalie Lassau, Saint-Mande (FR); Pierre Peronneau, Chateauneuf en Thymerais (FR); Valerie Rouffiac, Sucy en Brie (FR)

(73) Assignee: Institut Gustave Roussy (IGR), Villejuif (FR)

( * ) Notice: Subject to any disclaimer, the term of this patent is extended or adjusted under 35 U.S.C. 154(b) by 1157 days.

(21) Appl. No.: 12/520,519

(22) PCT Filed: Dec. 21, 2006

(86) PCT No.: PCT/IB2006/003742
§ 371 (c)(1),
(2), (4) Date: Nov. 9, 2009

(87) PCT Pub. No.: WO2008/053268
PCT Pub. Date: May 8, 2008

(65) Prior Publication Data
US 2010/0060644 A1 Mar. 11, 2010

(51) Int. Cl.
*A61B 8/08* (2006.01)
*A61B 8/06* (2006.01)

(52) U.S. Cl.
CPC .. *A61B 8/06* (2013.01); *A61B 8/481* (2013.01)
USPC .......................................... 345/440; 345/418

(58) Field of Classification Search
USPC .......... 345/418, 440; 600/431, 458, 414, 420, 600/438; 382/128, 131
See application file for complete search history.

(56) References Cited

U.S. PATENT DOCUMENTS

| | | | |
|---|---|---|---|
| 2004/0260178 A1 | 12/2004 | Kahn et al. | 600/437 |
| 2005/0085707 A1 | 4/2005 | Maria Korsten et al. | 600/407 |
| 2008/0187200 A1* | 8/2008 | Degani et al. | 382/131 |

(Continued)

FOREIGN PATENT DOCUMENTS

| | | |
|---|---|---|
| EP | 1 054 625 | 8/2007 |
| WO | 2004/110279 | 12/2004 |
| WO | 2006/067201 | 6/2006 |

OTHER PUBLICATIONS

Postert et al, "Contrast Agent Specific Imaging Modes for the Ultrasonic Assessment of Parenchymal Cerebral Echo Contrast Enhancement", The International Society for Cerebral Blood Flow and Metabolism, 2000, p. 1709-1716.*

(Continued)

*Primary Examiner* — Chante Harrison
(74) *Attorney, Agent, or Firm* — Seed IP Law Group PLLC

(57) ABSTRACT

A method and system process a test signal in medical domain by:—acquiring an input digital signal F(t) as a function of time t in the form of two-dimensional data, said signal F(t) resulting from the excitation, within a test substrate, of a substance adapted to emit a signal in response to said excitation;—modeling said input digital signal F(t) in function of a pre-established model;—possibly, generating an output digital signal I(t) made up from said modeling; wherein said modeling is based on the following model: (formula I) where the coefficients $a_0$, $a_1$, $a_2$, p, q, A and B are estimated on the basis of said two-dimensional data. The method and system are directed to the tumoral vascularization or tumoral angiogenesis detection in tumors.

20 Claims, 7 Drawing Sheets

(56) References Cited

U.S. PATENT DOCUMENTS

Figure 1:
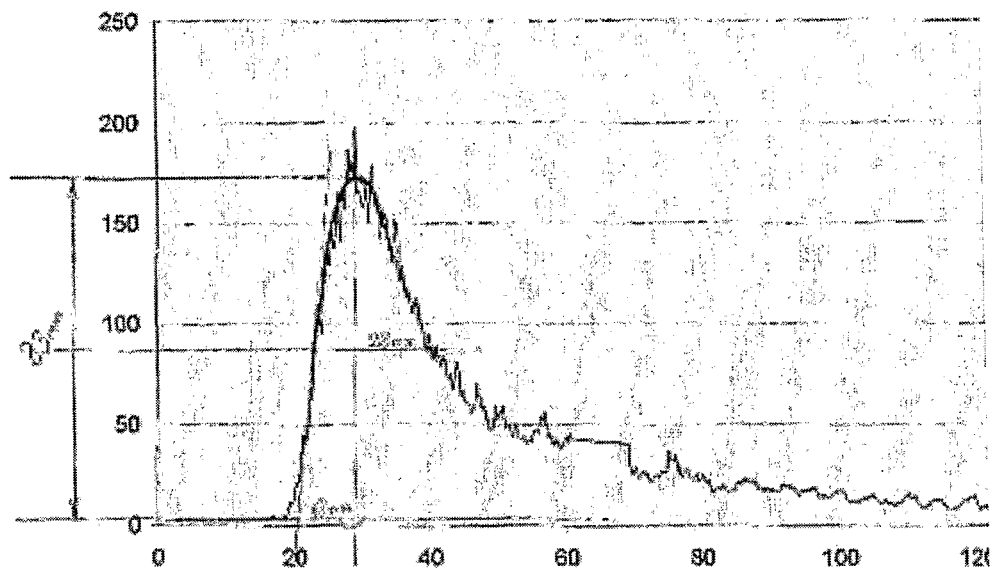

| | | | |
|---|---|---|---|
| 2009/0105582 A1* | 4/2009 | Dougherty et al. | 600/420 |
| 2009/0112097 A1* | 4/2009 | Kato et al. | 600/458 |
| 2011/0164796 A1* | 7/2011 | Hundley et al. | 382/128 |
| 2011/0245657 A1* | 10/2011 | Degani et al. | 600/420 |
| 2011/0257519 A1* | 10/2011 | Bj?rnerud et al. | 600/431 |
| 2012/0082352 A1* | 4/2012 | Hundley et al. | 382/128 |

OTHER PUBLICATIONS

Rosen et al., "DCE-MRI Demonstrates Antivascular Properties of Sorafanib in Metastic Hormone-Resistant Prostate Cancer", 2010, p. 4845.*

Krix et al., "Comparison of Intermittent-Bolus Contrast Imaging With Conventional Power Doppler Sonography: Quantification of Tumour Perfusion in Small Animals" Ultrasound in Med. & Biol. 29(8): 1093-1103, 2003.

Krogias et al., "Semiquantitative Analysis of Ultrasonic Cerebral Perfusion Imaging" Ultrasound in Med. & Biol. 31(8): 1007-1012, 2005.

Lucidarme et al., "Blood Flow Quantification with Contrast-enhanced US: "Entrance in the Section" Phenomenon-Phantom and Rabbit Study" Radiology 228(2): 473-479, Aug. 2003.

Wilkening et al., "Ultrasonic Assessment of Perfusion Conditions in the Brain and in the Liver" 2000 IEEE Ultrasonics Symposium: 1545-1548, 2000.

* cited by examiner

METHOD AND SYSTEM FOR QUANTIFICATION OF TUMORAL VASCULARIZATION

The invention relates to a method and corresponding system for processing a test signal in medical domain and notably a signal for quantification of tumoral vascularization. More specifically, the invention addresses a method for processing a test digital signal comprising following steps:

acquiring an input digital signal F(t) function of time t in the form of two-dimensional data (t, F(t)), said signal F(t) resulting from the excitation, within a test substrate, of a substance adapted to emit a signal in response to said excitation;

modeling said input digital signal F(t) in function of a pre-established model;

possibly, generating an output digital signal I(t) made up from said modeling;

The invention further relates to a method and corresponding apparatus of detection of tumoral vascularization within a test substrate.

The distribution of tissue or organ perfusion provides physiological and pathophysiological information.

In current clinical practice, several techniques are available to evaluate tissue perfusion. The most established techniques for the evaluation of tissue perfusion include, positron emission tomography (PET), magnetic resonance imaging (MRI) with contrast agents and ultrasonography. While PET and MRI are cumbersome techniques due to ionizing radiation or time-consuming examination, ultrasonography provides an efficient technique for measure repetition over a short period of time. In addition, the contrast agents used with the PET scan and MRI are not strictly intra-vascular agents and may spread rapidly into the interstitial space. On the contrary, ultrasound contrast agents are strictly confined to vessel lumen, and by virtue of that fact, are adequate for the evaluation of perfusion.

Ultrasound contrast agents are generally composed of microbubbles of gas encapsulated in a membrane. The change in acoustic impedance produced between these agents once injected and the surrounding environment allows one to increase the backscattered signal from blood. In this manner, ultrasonic intensity reflects the concentration of the contrast agent in the tissue and the amount of blood flow. Their use therefore improves the signal-to-noise ratio and thus facilitates the study of small deep-seated vessels or slow blood flow. Levovist (Schering®) and Sonovue® (Bracco) are two well-known contrast agents for ultrasonic application.

There are currently two ways of injecting contrast agents: via an infusion and a bolus injection.

The first method consists in delivering a constant concentration of the contrast agent in the individual before applying a "flash" high mechanical index in order to destroy the microbubbles. Then it is possible to study the kinetics of re-perfusion to obtain the initial concentration in the tissue. An example of this method is disclosed in the international patent application WO-2004/110279. The latter concerns a method for non-invasive quantification of tissue perfusion obtainable by a destruction-reperfusion process that provides a signal representative of local agent concentration during reperfusion. Then, at least one local tissue perfusion value is derived from this signal and made with correspondence to at least one value of at least one parameter of the function with S-shape characteristics. Examples of models used in this application are based on Gaussian, Rayleigh or lognormal functions.

The second method consists in injecting the contrast agent once (bolus) and observing its "wash in" and "wash out" signal in the tissue. The bolus method enables one to obtain a contrast uptake curve on which it is possible to extract specific perfusion parameters such as the dwell-in time of the contrast agent or the speed of the wash-out from tissue, which is not possible with the re-perfusion method. Moreover, the maximal amplitude of the curve obtained with the bolus method is more accurate than the maximal amplitude of the curve obtained with the re-perfusion method. From a practical point of view, this technique is also easier to implement in patients who come to an imaging unit. With both methods, tracking contrast uptake provides a curve of the signal intensity over time, an example of which is represented on FIG. 1.

It is important to model these contrast uptake curves thus obtained in order to have "un-noisy" curve for next use or exploitation, for example to extract objectively, reproducibly and if possible automatically parameters which quantify perfusion. The contrast uptake curves generally presents a first phase when the detected intensity quickly increases until a maximal value, then a second phase when the contrast uptake decreases more and more slowly. The model for the infusion technique appears to be well established with an exponential function: $I(t)=A(1-e^{(Bt)})$. On the other hand, the bolus model is not currently standardized. Very rarely do authors specify the model used. The main models that can be found in the literature are based either on Gamma-law distribution or on exponential equations. An example of such equations is provided below when compared to a test signal model according to the present invention.

Through experimentations and measurements, it has been observed that these Gamma-law distribution and exponential models don't describe in a correct way the kinetics of the bolus perfusion in tissue. It results in an unsatisfying degree of relevance concerning quantification of such perfusion. Therefore, there is a need from the prior art to provide more efficient technique on quantification of tumoral vascularization, basically to overcome limitation of state-of-the-art curves models. It is another need to efficiently remove test noise (provided by measuring equipment or external conditions—for example the patient while being breathing) from the signal.

It is one object of the invention to provide a solution to the above-indicated problems by modeling perfusion with a new-established model curve that fits with measures minimizing error gap between them (curve and measures) and then results in a more accurate use of the test curve, for example a better estimation of the parameters which quantify perfusion.

In one aspect, the invention provides an above-mentioned method wherein said modeling is based on the following model:

$$I(t) = a_0 + (a_1 - a_0) * \left( \frac{A + \left(\frac{t}{a_2}\right)^p}{B + \left(\frac{t}{a_2}\right)^q} \right)$$

and where the coefficients $a_0$, $a_1$, $a_2$, p, q, A and B are estimated on the basis of said two-dimensional data.

As developed above, the excitation may take various forms: positron emission for PET, magnetic field for MRI, ultrasound for ultrasonography.

In a preferred embodiment of the invention, the input signal F(t) correspond to detection of raw data.

The substance used in the method for the invention is adapted to the excitation type, that means it is sensitive to the used excitation nature in order to provide a response (an echo) to the excitation. As describe above, an ultrasound contrast agent fits to an ultrasonic excitation.

In such a way, the quantification of perfusion is non-invasive in regards with the substrate.

It can be shown (see detailed description) that this model performs a sharper estimation of the test signal regarding a bolus perfusion. Detailed benefits of this model are drawn up in the following description through the comparison between the invention and the state-of-the-art models.

The coefficients are highly dependent of the test data but don't derivate directly from the two-dimensional data. A solving process is performed on this model using said data, notably by determining said coefficients through the least-squares differences approach, that means the coefficients are adjusted in order to obtain a sum of the least-squares differences closest to zero between the test data and the modeled values.

According to the physical properties of the substance (e.g. contrast agent), the substrate or the measuring device, these coefficients can have highly variable values.

Generating the output signal I(t) can have various forms:
storage, in system memory, of the general model used for modeling and the parameters estimated. The stored data then comprise all information of signal I(t);
emission of the signal I(t) for graphical display, e.g. printed curve, display on video screen.

In one embodiment of the invention, the method further comprises a previous step for measuring comprising the acquisition of a temporal digital signal in the form of four-dimensional data $(t, x, y, f_{xy}(t))$ resulting from said excitation, where $f_{xy}(t)$ is a physical unit that is measured at time t in an area indexed (x, y) in said test substrate, and a step for transforming said four-dimensional data $(t, x, y, f_{xy}(t))$ into said two-dimensional data $(t, F(t)):F(t)=H(x, y, f_{xy}(t))$; H being the transformation function.

Therefore, the invention enables an investigation on an area of interest as a whole with actual measuring equipment. Indeed, the medical equipment measures a physical unit (e.g. energy, electrical current, voltage, electric field, magnetic field, . . . ) at several locations of the substrate to be observed. As the main application of the invention is concerned, i.e. quantification of tumoral vascularization, the medical equipment is one type of ultrasonograph (ultrasonic scanner, ultrasonic system) and the test signal represents the echoes of generated ultrasonic waves by the substrate at several locations (defined as pixels in the rendered image).

As an enhancement of the method above, said transformation computes a mean linear power F(t) of the values $f_{xy}(t)$ over a defined zone of said substrate, said zone being composed of a set S of locations (x, y) and said mean linear power F(t) being:

$$F(t) = \frac{\sum_S f_{xy}(t)}{\text{card}(S)}$$

where Card(S) is the number of locations (x, y) in said set S, and $$\sum_S$$

is a sum over the set S.

Mainly, the defined zone is the area of interest that an operator defined initially on which a measure has to be done. As introduced previously, this area is made of pixels whose coordinates in the resulting image are the indexes (x, y). Several ways to define this area are available to the invention, from a computer-implemented method based on edge detection, to a manual definition of the zone by the operator, for example drawing a specific shape delimitating this zone. In medical applications, a common shape is a circle or an oval, by any of more complex shapes can be used. Once defined by the operator, the zone S is composed of a number of pixels (x, y), what we name Card(S).

In another enhancement, acquiring said signal in the form of four-dimensional data is made through ultrasonic means.

In a specific embodiment, said signal F(t) results from the administration of said substance within said test substrate prior to the excitation. Possibly, the substance comprises a contrast agent. As explained above, this administration can take the form of a bolus to provide ultrasonic contrast agent in the substrate.

The invention can be applied to any substrate chosen from the group comprising a human or animal subject, a tissue extract, a blood sample.

To achieve a fast and accurate estimation of the coefficients $a_0$, $a_1$, $a_2$, p, q, A et B on the basis of the test data, the estimation of the coefficients is based on the minimization of the sum of the least-squares differences between said two-dimensional data and said model.

This solving of the model to estimate the coefficients can easily be computer-implemented through software or any existing solving functions of known mathematical software.

It is also an object of the invention to provide a method of tumoral vascularization or tumoral angiogenesis detection in a test substrate comprising the steps of:

(i) determining at least one parameter (test parameters) from the modeling performed according the method of any preceding claim when resulting from the excitation of a contrast agent present in said test substrate;
wherein at least one parameter is chosen from the group comprising the maximal amplitude $PI=I_{max}-I_{min}$ of said output signal I(t), where $I_{max}$ and $I_{min}$ are respectively the maximum and minimum values of I(t), the required time ($T_{PI}$) for the output signal I(t) to reach its maximal amplitude PI from the beginning ($T_L$) of the contrast uptake, the mean transit time (MTT) corresponding to the time during which the value I(t) of the output signal is higher than the mean value $(I_{max}+I_{min})/2$.

Other test parameters can also be chosen. Among them the area under the curve, the slope of the wash in, the area under the wash in and the area under the wash out are parameters suitable for tumoral vascularization or tumoral angiogenesis detection.

(ii) comparing said at least one determined parameter with reference parameters.

In regards with the model according to the present invention, these three parameters appear to be the most accurate parameters to quantify perfusion by contrast agents. Even if they can be used alone, they are generally used in combination. The best results in tumoral vascularization detection are achieved when using all three parameters together in comparison to said reference parameters.

The time $T_L$ corresponding to the beginning of the contrast uptake represents a latency time between the administration of the contrast agent in the test substrate at $t=T_0$ and the beginning of the contrast uptake at $t=T_L=T_0+T_{LATENCY}$ ($T_{LATENCY}$ is the latency delay).

The result of the comparison is used for several applications, for example, improving the coefficients $a_0$, $a_1$, $a_2$, p, q, A et B, detecting an evolution of the tumoral vascularization or tumoral angiogenesis in the substrate.

In one embodiment, said reference parameters are parameters which are determined from a modeling performed according to the method for processing as described above when resulting from the excitation of said contrast agent present in a reference substrate. This embodiment has the advantage to provide test parameters (from test substrate) in a same way than reference parameters. The comparison thereof results in a higher accuracy.

In an enhancement, said reference substrate is chosen from the group comprising:
  a substrate issued from a healthy subject, which provides objective reference values;
  said test substrate at a time t prior to said excitation of test substrate.

In the second alternative, as the reference parameters are issued from the same substrate than the test substrate, but at a prior time, the invention enables an estimation of the tumoral vascularization evolution within the same substrate. Practically, test parameters are determined at various moments in time, either with the same modeling used for all moments or a new estimated modeling (new estimation of the corresponding coefficients) for each moments, and compared one another to detect a change in tumoral vascularization of the test substrate.

As described above, the method can further comprise, prior to step (i), a step of injecting said contrast agent in said test substrate.

In a second aspect, the invention relates to a system for processing a digital signal comprising:
  means for acquiring an input digital signal F(t) as a function of time t in the form of two-dimensional data (t, F(t)) resulting from the excitation, within a test substrate, of a substance adapted to emit a signal in response to said excitation. These means for acquiring are generally a software module of a more general software system. This specific module can receive the input signal from a reader, like a probe or a sensor. As the module can be programmed to specific treatments, it is adapted to deal with (even transform) the input signal in two-dimensional form. As an alternative, a hardware implementation of this module can easily be achieved with general knowledge about the correspondence between software processing and hardware structure;
  means for modeling said input signal F(t) in function of a pre-established model. Such modeling means comprise in a first part a memory storing the below pre-established model and, in a second part, a software or hardware structure adapted to solve this model in function of the acquired two-dimensional data to minimized the error gap as mentioned above. A computer implementation including ROM memory is totally adapted to perform these means. Software solvers, often specific functions in mathematical softwares like Mapple® or Matlab®, can be used.
  a generator of an output digital signal I(t) made up from said modeling. This generator can perform a storage in memory of the estimated below coefficients. According to an alternative, the generator is an emulator that provides a printer or a screen or any displaying means with a curve representing said signal I(t).

In the system, said pre-established model is:

$$I(t) = a_0 + (a_1 - a_0) * \left( \frac{A + \left(\frac{t}{a_2}\right)^p}{B + \left(\frac{t}{a_2}\right)^q} \right)$$

where $a_0$, $a_1$, $a_2$, p, q, A and B are coefficients to be estimated, and said means for modeling comprises a solver to estimate said coefficients on the basis of said two-dimensional data.

To adapt the invention to the known medical measuring equipments, said acquiring means comprises an ultrasonic probe adapted to excite said substance and read the echoes emitted by the substance in response to the excitation. As the measures are made with analog apparatus, the acquiring means also comprises converters from analog signal (received from the substance) to digital signal for further processing.

In one embodiment, said acquiring means is adapted to acquire a temporal digital signal $f_{xy}(t)$ in the form of four-dimensional data (t, x, y, $f_{xy}(t)$) resulting from said excitation, where $f_{xy}(t)$ is a physical unit that is measured at time t in a location indexed (x, y) in said test substrate, and said acquiring means further comprising means for transforming said four-dimensional data (t, x, y, $f_{xy}(t)$) into said two-dimensional data (t, F(t)):F(t)=H(x, y, $f_{xy}(t)$); H being the transformation function.

It is also an object of the invention to provide an apparatus for tumoral vascularization or angiogenesis detection in a test substrate, said apparatus comprising:
  a system as described above to model an acquired signal in response to the excitation of a contrast agent in said substrate;
  means for determining at least one parameter from said modeling performed by said system, said at least one parameter being chosen from the group comprising the maximal amplitude $PI=I_{max}-I_{min}$ of said output signal I(t), where $I_{max}$ and $I_{min}$ are respectively the maximum and minimum values of I(t), the required time ($T_{P1}$) for the output signal I(t) to reach its maximal amplitude PI from the beginning ($T_L$) of the contrast uptake, the mean transit time (MTT) corresponding to the time during which the value I(t) of the output signal is higher than the mean value $(I_{max}+I_{min})/2$. This means for determining can be a software or hardware structure configured/programmed to calculate said above-mentioned parameters from the output signal previously generated (or from the modeling when the coefficients has been estimated). An alternative can be the use of a graphical representation in order to the operator to perform direct measurements on this representation and calculate the parameter(s);
  a comparator adapted to compare said at least one parameter with reference parameters. As the parameters are generally provided as values, well-known comparators between two or more values can be used to achieve the comparison according to the invention.

An application of the present invention is addressed to the quantification of tumor perfusion for angiogenesis using ultrasound contrast agent. The following description of the invention is based of this non-limiting application.

Another preferred application of the present invention is the quantitative evaluation of therapies impact on tumoral microvascularization.

This invention will be better understood thanks to the following description explaining the physical basis of the invention and based on the enclosed drawings showing a preferred embodiment of the latter as a non-limitative example of implementation.

Figure 2:
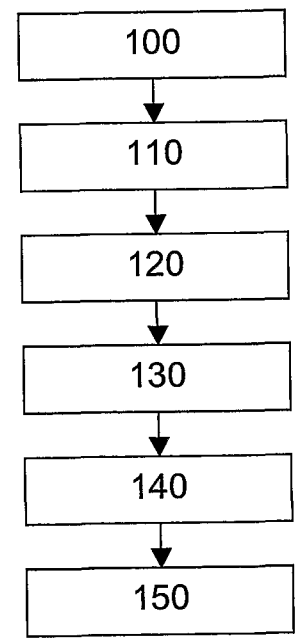
Figure 3:
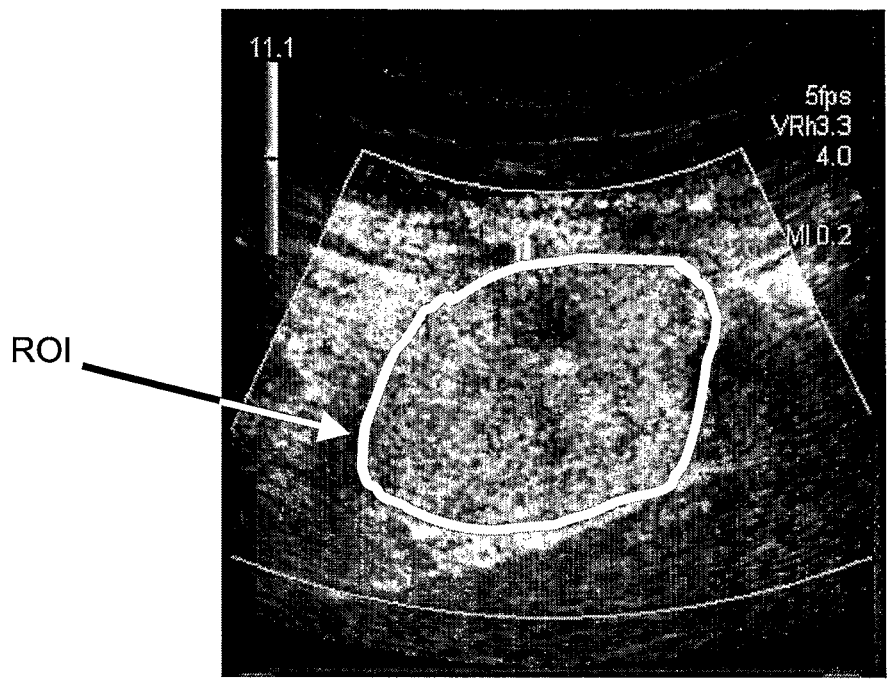
Figure 4:
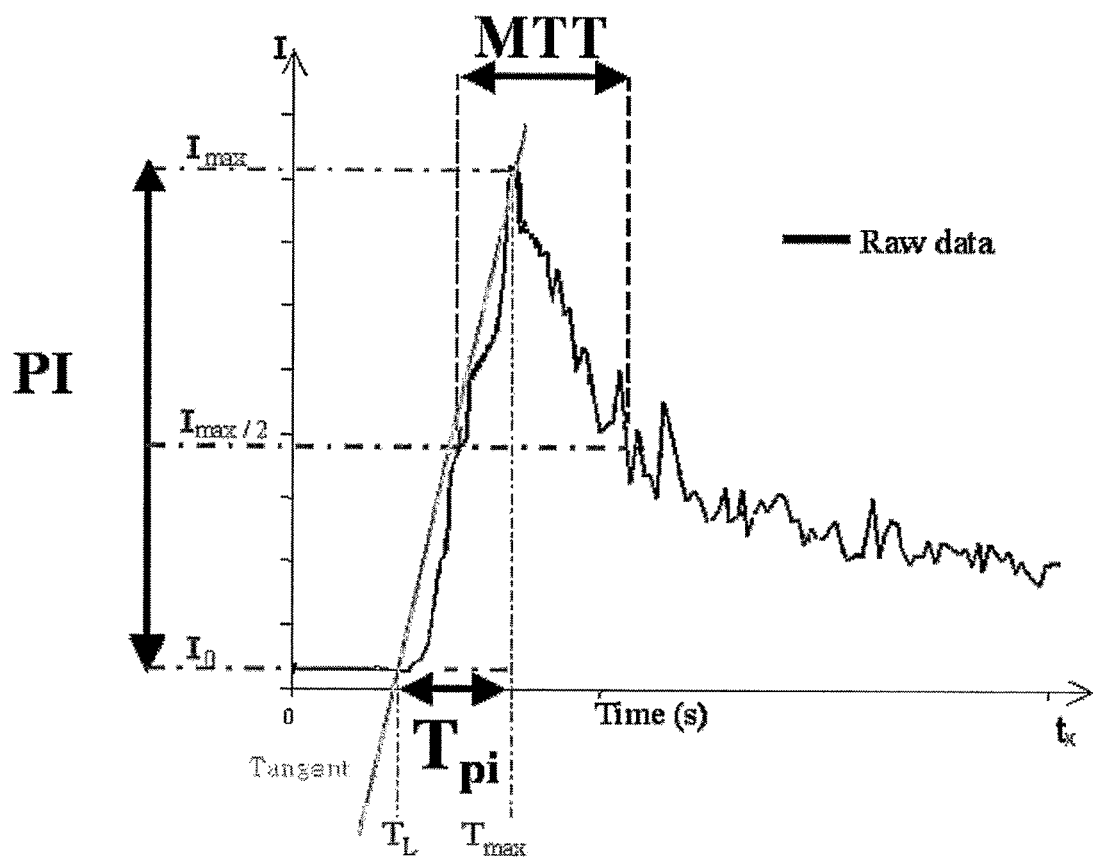
Figure 11:
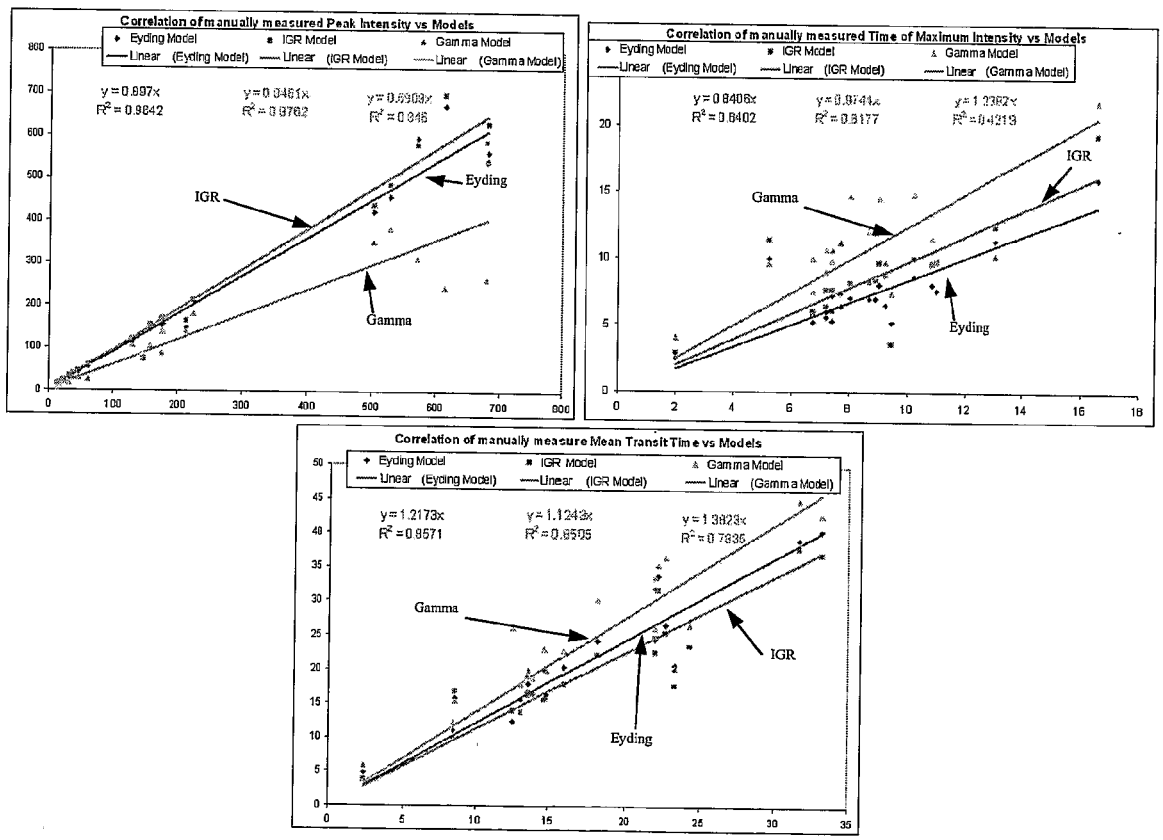
Figure 12:
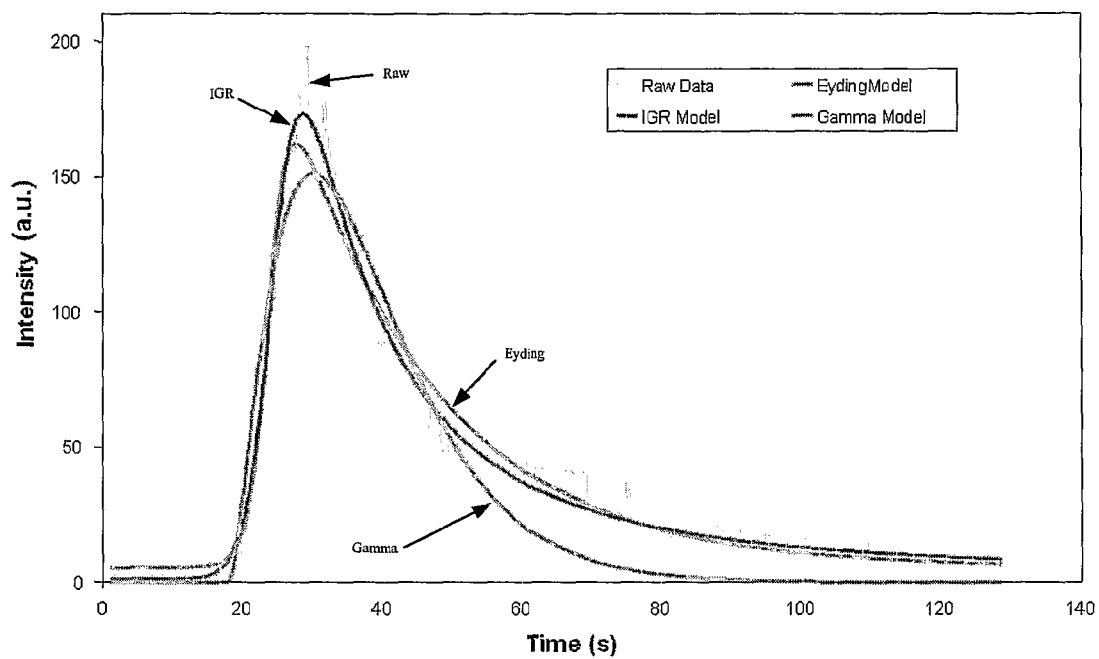
Figure 13:
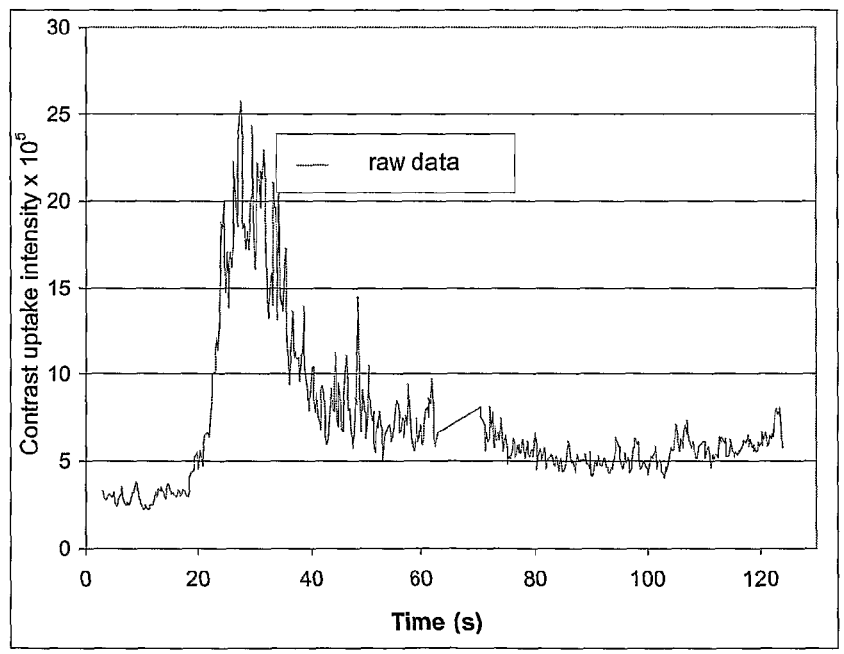

In the enclosed drawings:

FIG. 1 is a graph showing an example of contrast uptake curve over time,

FIG. 2 is diagram representing the successive steps of a method implementing the invention, FIG. 3 illustrates a region of interest ROI in a ultrasonic imaging, FIG. 4 is a graph of contrast uptake curve showing the perfusion parameters used in the present invention, FIG. 5 to FIG. 12 are diagrams and graphs comparing and illustrating the performance of the model (noted IGR model in the figures) according the present invention in regards to the state-of-the-art models, and FIG. 13 is a graphical plot of a contrast uptake curve.

The following description is directed to a general system and experimentations that have been performed in order to demonstrate the efficiency of the invention and especially the model according to the invention, compared to the know approaches.

Material and Methods

Patients

The experimentations have been performed on six patients. Twenty perfusion curves were selected in these six patients at different periods of their tumor growth. This choice allowed to acquire a broad spectrum of contrast uptake distributions that may be observed in the clinic before and during antivascular therapy.

Four patients presented with secondary hepatic metastases and two others presented with less well localized abdominal masses.

Acquisition of Perfusion Curves

Contrast Agent

The contrast agent used was Sonovue® (Bracco, Italy). It is composed of microbubbles of sulphur hexafluoride stabilized in a phospholipidic shell. Sonovue® is reconstituted with a solution of sodium chloride (5 ml) just before use to obtain a concentration of 8 µ/ml.

This contrast agent has been injected in the patients at time $T_0$ (step 100, FIG. 2)

Several imaging modes exist that capitalize on the physical behavior of contrast agents and particularly detect the nonlinear harmonic signal emitted by the microbubbles resounding at a low mechanical index (MI=0.1-0.2). Several detection techniques are under development in industry. Nonetheless, the most widespread sequence is pulse subtraction based on the echoes of 2 phase-inverted pulses. Summing the signals received after the emission of these 2 phase-inverted pulses allows one to exclusively capture the harmonic signal emitted by the microbubbles. The magnitude of the resulting wave is very low if the emitter behaves in a linear manner (such is the case with tissues) but it is very high if the emitter is not linear (which is the case with microbubbles).

Ultrasound

The studies were conducted on a Aplio ultrasound machine (Toshiba Medical Systems), equipped with two broadband probes with a central frequency range of 3-4 MHz for the study of deep-seated organs and 8-12 MHz for the study of more superficial organs. The ultrasound examination (step 110, FIG. 2) was conducted in several steps for each patient.

B Mode

In this imaging mode, the maximal axial resolution of the probes is 0.11 mm and the maximal lateral resolution is 0.17 mm. The 3 largest diameters of the tumor were measured: transversal, longitudinal, and thickness. As the tumor approximates an ellipsoid, its volume is calculated in the following manner: (thickness×length×width)×π/6 mm$^3$.

Vascular Recognition Imaging® (VRI) Mode

Tumor perfusion data and contrast agent kinetics were measured using Vascular Recognition Imaging (VRI) developed by Toshiba and based on the detection of ultrasound contrast microbubbles (step 120, FIG. 2).

The mechanical index used in this mode is very low (MI=0.1) and it ensures that the contrast agent microbubbles (SonoVue®, Bracco) remain intact without bursting. It is possible to use their nonlinear vibration property with this mechanical index.

The VRI Mode combines three exploration modes at a low mechanical index (MI=0.1) on one and the same image:

B mode allows the visualization of tissues

The Advanced Dynamic Flow mode allows one to visualize the direction of blood flow in vessels The contrast detection mode based on pulse subtraction enables the detection of perfusion The harmonic signal emitted by the microbubbles is coded in blue or red respectively for the macrovessels harboring microbubbles that are moving away from the probe or those moving towards it and in green for almost static microbubbles in microvessels, thus providing imaging of vessels and of perfusion.

The new technological capability, VRI allows one:

to increase the sensitivity of microvessel detection to superimpose the harmonic image onto the baseline image of tissues for better anatomical localization unlike the pulse subtraction method which is used more frequently for imaging with contrast agents to record contrast uptake kinetics in raw data For each examination, a digital sequence (5 images/second) was recorded in linear data (raw data: uncompressed before standard video-visualization) over 180 seconds after an intravenous injection of a 5 ml bolus of contrast agent. The increase in contrast uptake thus recorded during the passage of microbubbles is linearly linked to the number of particles of contrast agent detected in the tissue. This signal is therefore directly linked to the perfusion of this tissue. The signal intensity produced by the contrast agents is expressed in arbitrary units for each image of the recorded sequence. Each patient had his/her examination with the same machine settings over time.

CHI-Q Software® (Toshiba)

The quantification of perfusion and contrast uptake kinetics was performed (step 130, FIG. 2) using the prototype of a dedicated software (CHI-Q®), in the framework of a partnership with Toshiba. From raw data recorded for each image in the sequence, this software calculates contrast uptake in a region of interest (ROI) encompassing the entire tumor section chosen by the clinician. This enhancement is expressed in linear power (arbitrary units).

Using the digital sequences acquired in VRI mode after injection of SonoVue, the CHI-Q software calculates the mean linear power (in arbitrary units) emitted by the contrast agent microbubbles (FIG. 1) within the ROI outlined by the operator. This ROI represents precise contouring of a liver tumor (FIG. 3)

The CHI-Q software also allows semi-automatic tracking of the ROI during sequence acquisition. This capability is very useful for correcting artifacts caused by heavy breathing which may displace the lesion during sequence acquisition.

Quantification of Perfusion Parameters

In order to be able to extract the perfusion parameters from the contrast uptake curve, a number of factors were used to characterize it (FIG. 4):

$I_0$ (or $I_{min}$) is the baseline line intensity without contrast agent $I_{max}$ is the intensity when contrast uptake is maximal To take into account variations in the bolus injection, all times were normalized according to the latency time ($T_L$) defined as the time between the injection of the product and the beginning of contrast uptake. The $T_L$ is defined as the meeting point between the vertical line y=Io and the tangent to the perfusion curve at the $I_{max/2}$ point.

Three parameters were extracted from the perfusion curves: the maximal intensity (PI) defined as the difference between $I_{max}$ and $I_0$; the time required to attain the maximal intensity ($T_{PI}$) defined as the difference between $T_{max}$ and $T_L$, and the mean transit time (MTT). The MTT is the time during which contrast uptake was higher ($I_{max}+I_0$)/2.

To achieve this extraction of parameters, a treatment of the curves is made as following.

Treatment of Curves

Recovery of Reference Perfusion Parameters

We wanted to compare the PI, $T_{PI}$ and MTT perfusion parameters obtained after modeling the curves with the reference data. These reference data were acquired by manually plotting the twenty curves on an A4 format sheet of millimetric graph paper (FIG. 1). The perfusion curves generated by Excel®, based on raw data from the CHI-Q software, were printed onto millimetric graph paper. Each perfusion curve was manually plotted in order to calculate the three perfusion parameters. The three perfusion parameters (PI, $T_{PI}$ and MTT) were manually measured on each raw data curve three times on different days.

Optional Filtering

An optional filtering can be applied to the values of quantification in order to smooth the perfusion curve. Such a filtering can be based on a convolution nucleus of size 3, 5 or 9, for example. However, a convolution filter is known to deteriorate the information values even if the resulting curve appears smoother.

Models

Three equations were chosen to model the perfusion curves including the model according to the present invention. The first equation is based on Gamma-law distribution:

$$I(t) = a(t-t_a)^c * \exp[-b(t-t_b)]$$

where I(t) is the (signal) intensity of contrast uptake after injection of the contrast agent, t is the time elapsed after injection of contrast agent, $t_a$ is the latency time and a, b, c are defined as arbitrary parameters. This equation will henceforth be called the Gamma equation.

The second equation, mainly used to study brain perfusion and first published in the year 2000 by Postert et al is as follows:

$$I(t) = a_0 + a_1 \frac{e^{-a_2 t}}{1 + e^{-a_3(t-t_0)}}$$

where I(t) is the (signal) intensity of contrast uptake after injection of the contrast agent, t is the time elapsed after the injection of contrast agent, $t_0$ is the latency time, $a_0$ is the intensity before the arrival of the contrast agent, $a_1$ is a scale factor, $a_2$ is a coefficient for the decline in contrast uptake after the peak intensity and $a_3$ is a coefficient for an increase in intensity. This equation will henceforth be termed the Eyding and Postert equation.

Finally, the third equation concerns the model according the present invention and associates a sigmoid equation with Postert's works which gives the following model function:

$$I(t) = a_0 + (a_1 - a_0) * \left( \frac{A + \left(\frac{t}{a_2}\right)^p}{B + \left(\frac{t}{a_2}\right)^q} \right).$$

where:

I(t) is the intensity of contrast uptake after injection of the agent, t is the time after the injection of the contrast agent, $a_0$ is the intensity before the arrival of the contrast agent, q is a coefficient for the decline in contrast uptake after the peak intensity, p is a coefficient for an increase in intensity, $a_1$ is linked to the maximal value of contrast uptake, $a_2$ is linked to the time to the rise to the maximal intensity, and A and B are arbitrary parameters.

This equation is henceforth called the IGR equation.

The raw values from the quantification were modeled on the basis of this equation (step 140, FIG. 2) by calculating the coefficients.

Solving Approach

Practically, the data to be modeled are provided through text files 15 generated by the Aplio system. These files comprises the linear contrast uptake data with values around 10-6 in function of time with an interval of 0.2 seconds between two successive measures. The files generally comprises as a maximum 60 sec. of recording.

The data are extracted from these files to draw up a graph in Excel® (see FIG. 14). As these data are "noisy", it is difficult to extract the perfusion parameters from the plotting. That's why the modeling of this curve is processed according to the invention.

The contrast uptake data are previously multiplied by $10^5$ in order to work with significant values (too low values are pernicious for further 25 solving). The coefficients $a_0$, $a_1$, $a_2$, p, q, A and B of each of the three equations are adjusted in order to obtain a sum of the least-squares differences closest to zero between raw values and modeled values using the Solver program in Excel®. This adjustment is done for the twenty curves selected.

The solver of Excel is a command that permits to modify values of cells in the spreadsheet in order to see how they affect the results of formulae in the spreadsheet. By successive modification of values of a set of cells (the coefficients cells for the present resolution), the solver can find optimal values for a formula (sum of the least-squares differences in one embodiment of the present invention) of a cell.

A preliminary setting is done with $a_0$=value of the signal at the beginning of the recording; $a_1$=maximal value of the signal through the total recording; and $a_2$=rising time between the beginning of the recording and the time when the maximal value $a_1$ is reached.

A single constraint on coefficients is indicated to the solver: $a_0$ cannot be negative.

Additional constraints are set to the solver:

maximum time to solve: 100 sec, precision step: 0.000001, convergence degree: 0.0001 (that means the solver will stop its resolution when it modifies the coefficient values within this range around a value).

The solver is then executed. It is based on the non-linear optimizing code "Generalized Reduced Gradient" (GRG2), information of which is provided on http://www.emse.fr/~beaune/solveur/Algo.html Then, the three perfusion parameters were automatically extracted (step 150, FIG. 2) from the three model perfusion curves.

Statistical Analysis of Data

The Mann-Whitney non-parametric test was used to test whether two groups of data were independent or not. Correlation was analyzed with Spearman's Rank correlation test.

These tests were done with the Stata software (Stata 8.0, Corporation, USA). A p value of <0.05 was considered statistically significant.

The first test was performed to determine whether the difference between the three perfusion parameters (PI, $T_{PI}$ and MTT) manually measured on the raw data curves was significant or not. The same test was performed for data obtained from the three perfusion parameters manually measured on five curves with the low pass filters, size 3, 5, and 9.

A comparison was performed on the perfusion parameters obtained on the raw data and filtered curves. Then, another comparison was performed on data from raw data curves and data extracted from model curves. Finally, after calculating the error between the reference data (raw data curves) and the modeled data, these error coefficients were compared $$\text{error} = \left|1 - \left(\frac{\text{model\_value}}{\text{reference\_value}}\right)\right| \times 100$$

We then correlated raw data and data extracted from the models in order to determine the Spearman coefficient expressing the error factor between the models and the raw data.

Results—Study of Model Equations

Figure 5:
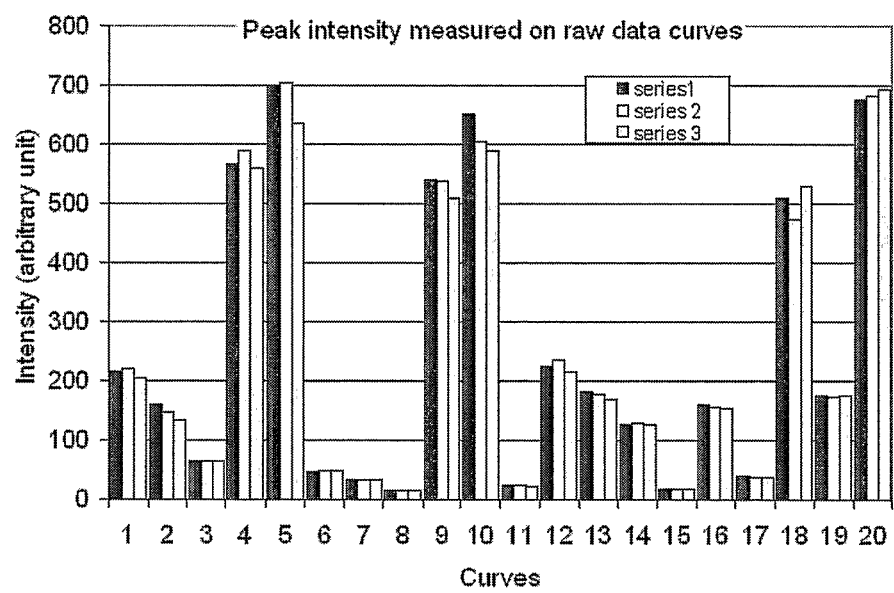

Comparison of Three Perfusion Parameters Measured Manually on the Raw Data Perfusion Curves No significant difference was found between the three manual measurements of the peak intensity on the twenty curves (p=0.8287) (FIG. 5)

Figure 6:
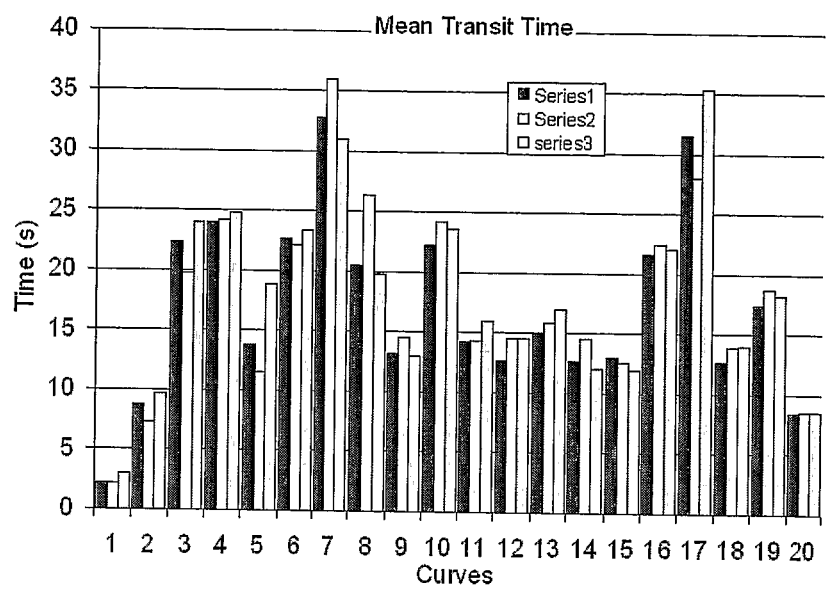

Likewise, no significant difference was found between the three manual measurements of the mean transit time (p=0.6455) (FIG. 6)

Figure 7:
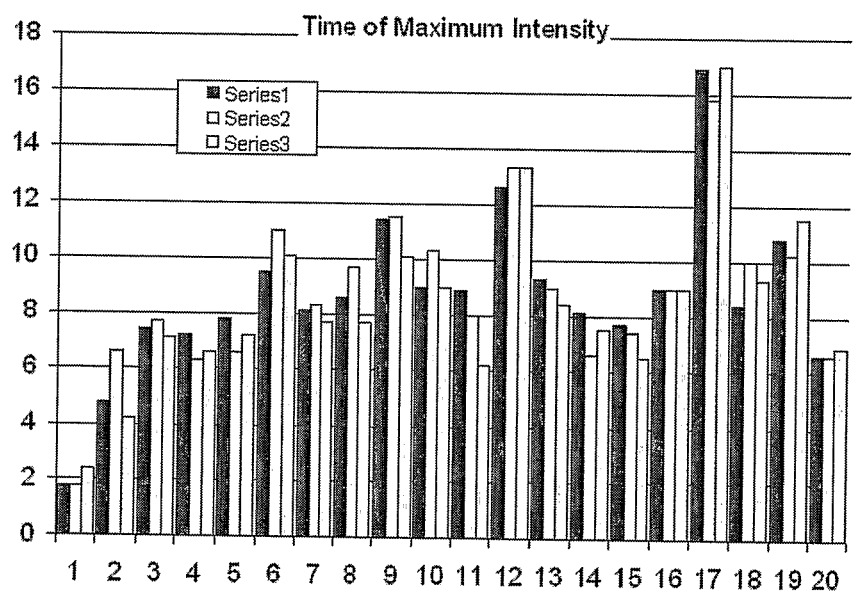

Finally, no significant difference was observed for the manually measured time of maximum intensity values (p=0.4648) (FIG. 7).

Figure 8:
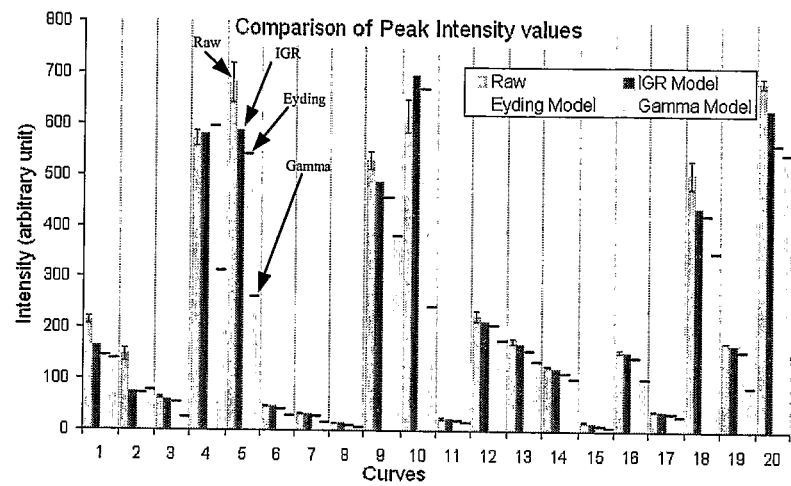

Comparison Between the Reference Perfusion Parameters (Raw Data Values) and Those Obtained With the Three Models:

For the peak intensity, the three models exhibited values that were very often slightly below the reference values with respectively for the IGR, the Eyding and the Gamma models. However, no significant difference was observed between the reference data and those yielded by the IGR model (p=0.7251), Eyding (p=0.5518) and Gamma (p=0.2134) (FIG. 8).

Figure 9:
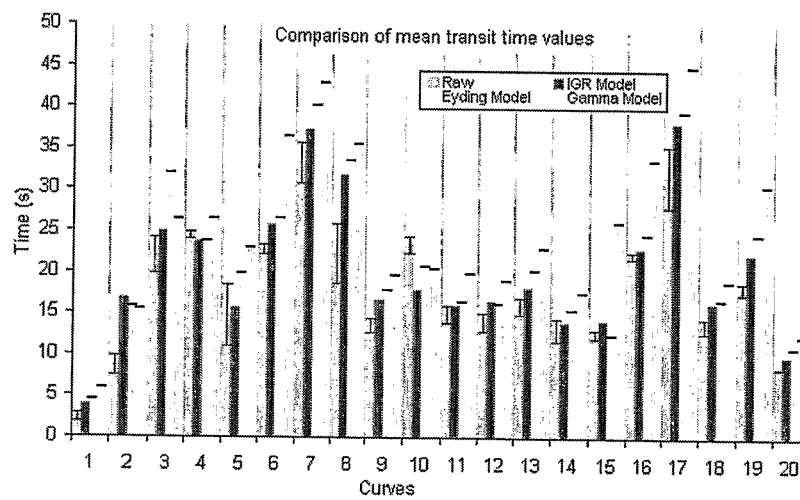

For the comparison of the mean transit time, no significant difference was observed between the reference data and the IGR and Eyding models; (p=0.1941) and (p=0.1298) respectively. In contrast, the values obtained were very overestimated in relation to the raw values with the Gamma model (p=0.0161) (FIG. 9).

Figure 10:
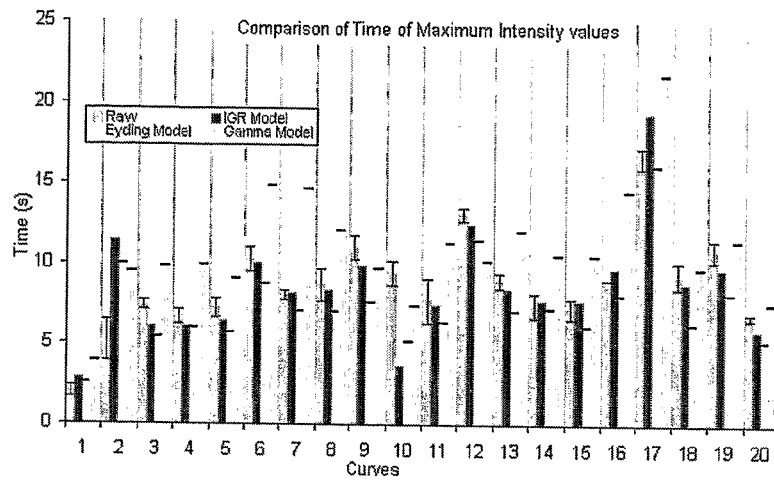

Finally, for the maximum intensity time values, only the IGR model remained in the reference area with no significant difference with the values measured manually (p=0.7867). However, there was a major difference for two curves (curves 2 and 10). There was a significant difference between the reference values and those yielded by the Eyding (p=0.0337) and Gamma (p=0.0068) models (FIG. 10).

The comparison of the error rates obtained with the three models for the three perfusion parameters revealed that the three models exhibited significantly different error rates (Table 1 below). Thus the data obtained with the IGR model were very different from those obtained with the Eyding and Gamma models which themselves also exhibited different error rates.

TABLE 1

Results of the test comparing error rates between the three models for the three perfusion parameters studied.

| | Peak Intensity | Transit Time | Intensity Time |
|---|---|---|---|
| IGR vs Eyding | 0.0186 | 0.1105 | 0.0102 |
| IGR vs Gamma | <0.0001 | 0.0004 | 0.0006 |
| Eyding vs Gamma | <0.0001 | 0.0068 | 0.0144 |

According to the regression line, the IGR model exhibited an error rate of −5.4% for the peak intensity in relation to the reference data. For the Eyding and Gamma models the error rate was respectively −10.3 and −40.9%. For the mean transit time, the error rate was +12.4% for the IGR model, +21.7% for the Eyding model and +38% for the Gamma model. Finally, for the maximum intensity time, the error rate was −2.5%, −15.-% and +23.9% for the IGR, Eyding and Gamma models respectively (FIG. 11).

The findings obtained with the three models on the twenty curves allowed us to note that the Eyding model found it difficult to attain accurate peak intensity and that the Gamma model found it difficult to model the descending slope of contrast uptake (FIG. 12).

CONCLUSION

Today, thanks to the recent association of ultrasound techniques (use of harmonics) with contrast agents, it is possible to obtain perfusion curves for tissues under study. These data thus collected are of paramount importance for hemodynamic information concerning such tissue.

The problem at present is to be able to extract perfusion curve parameters objectively. These data therefore require treatment. They can be measured directly or via a model. Direct quantification is difficult because the data obtained are "noisy" or can exhibit major artifacts mainly caused by the patient's breathing. Modeling or filtering these data is therefore necessary to automatically obtain reliable quantification which is also rapid and not operator dependent.

Modeling perfusion curves was only done on raw data without any prior treatment of data. The least-squares method permits to adjust the coefficients of model equations. Thanks to this approach, there is no subjective implication on the part of the operator when searching for the best coefficients. The only requirement to obtain the best possible coefficient is to specify a range at the outset. Practically, the coefficients provided at the outset are automatically extracted from the raw curve which allowed us to give an order of magnitude.

We were therefore able to, first specify the error rate of the different models for the three perfusion parameters we had selected. Although we sometimes found highly developed theoretical demonstrations of models presented in the literature, we were unable to find information on the error rate of these models. Indeed, the authors directly apply their equation to a study without indicating an error margin that we would have been able to compare with our data.

Secondly, studying the three models allowed us to compare them to each other. We were able to characterize the stumbling blocks while modeling a perfusion curve. Thus the Gamma model is extremely limited when the descending slope of the perfusion curve is not steep. In that case, the curve obtained is forced to spread out and to provide a low peak intensity value in relation to the raw data and a very poorly modeled descending slope. For the equation according to the present invention, the model which yielded the best results, we found that the peak intensity was slightly lower than in reality but to a lesser extent than with the other models. The data obtained after modeling the transit time were always greater than those of the raw data. The only plausible explanation for this point is that it is difficult for these equations to adequately model the ascending and descending slopes of the perfusion curve simultaneously, the latter slope being generally longer than the former.

The whole study was performed with perfusion curves exclusively acquired on unique tumor sections. To provide a more sharp result, a complete quantification of perfusion on the entire volume of the tumor may increase the accuracy of these perfusion parameters.

Other imaging techniques are appropriate and accurate for the dynamic evaluation of perfusion. Ultrasound is however easier to apply for the study of rapid hemodynamic changes with results that are at least equivalent to those of MRI and the PET scan. Furthermore, the short duration of ultrasound examinations offers the possibility of studying changes very rapidly after an antivascular treatment. It is also possible to use it repeatedly over short time intervals. In addition, the widespread availability of ultrasound machines in clinical radiology as well as the lack of adverse effects on the patient, make this method a simple technique for determining the efficacy of antivascular therapies in clinical studies. Also, the recent availability of contrast agents for use with advanced detection modes (for example VRI) and perfusion software capable of working on linear data, opens the possibility of attaining objective and accurate quantifications in studies of the kinetics of drug activity on tissue perfusion.

The invention claimed is:

1. A method:
acquiring a first input digital signal F(t), which is a function of time t, in the form of two-dimensional data (t, F(t)), said signal F(t) resulting from an excitation, within a test substrate, of a substance adapted to emit a signal in response to said excitation;
modeling said first input digital signal F(t) in function of a model;
generating a first output digital signal I(t) made up from said modeling;
wherein said modeling is based on a model of the type:

$$I(t) = a_0 + (a_1 - a_0) * \left( \frac{A + \left(\frac{t}{a_2}\right)^p}{B + \left(\frac{t}{a_2}\right)^q} \right)$$

wherein:
the modeling and generating are performed using a computing device;
coefficients $a_0$, $a_1$, $a_2$, p, q, A and B are estimated on the basis of said two-dimensional data;
$a_1$ is a coefficient related to a value of a maximum of the output digital signal I(t);
$a_0$ is a value of the output digital signal I(t);
$a_2$ is a coefficient related to a time of the maximum of the output digital signal I(t);
p is a coefficient related to an increase in the output digital signal I(t);
q is a coefficient related to an decrease in the output digital signal I(t); and
A and B are arbitrary parameters.

2. A method according to claim 1, further comprising:
acquiring a temporal digital signal in the form of four-dimensional data (t, x, y, $f_{xy}(t)$) resulting from said excitation, where $f_{xy}(t)$ is a physical unit that is measured at time t at a location indexed (x, y) in said test substrate, and
transforming said four-dimensional data (t, x, y, fxy(t)) into said two-dimensional data (t, F(t)), wherein said transforming includes computing the first input digital signal F(t) as a function of y and fxy(t).

3. A method according to claim 2, wherein said transforming includes computing the first input signal F(t) as a mean linear power of the values $f_{xy}(t)$ over a defined zone of said substrate, said zone being composed of a set S of locations (x, y) and said mean linear power being equal to:

$$F(t) = \frac{\sum_S f_{xy}(t)}{\text{card}(S)}$$

where card(S) is a number of locations (x, y) in said set S, and $$\sum_S$$

is a sum over the set S.

4. A method according to claim 2, wherein acquiring said signal in the form of four-dimensional data is made using an ultrasonic device.

5. A method according to claim 1, wherein said signal F(t) results from the administration of said substance within said test substrate prior to the excitation.

6. A method according to claim 1, wherein said substance comprises a contrast agent.

7. A method according to claim 5, wherein said contrast agent is an ultrasound contrast agent administrated by bolus in said test substrate.

8. A method according to claim 1, wherein said test substrate is chosen from the group consisting of a human or animal subject, a tissue extract, a blood sample.

9. A method according to claim 1, wherein said estimation of the coefficients is based on the minimization of the sum of the least-squares differences between said two-dimensional data and said model.

10. A method according to claim 1, comprising:
detecting tumoral vascularization, the detecting including:
(i) determining at least one parameter from the modeling when resulting from the excitation of a contrast agent present in said test substrate, wherein the determining includes choosing the at least one parameter from the group comprising the maximal amplitude $PI=I_{max}-I_{min}$ of said output digital signal I(t), where $I_{max}$ and $I_{min}$ are respectively the maximum and minimum values of I(t), the time for the output signal I(t) to reach its maximal amplitude PI from the beginning of the contrast uptake, the mean transit time corresponding to the time during which the value I(t) of the output signal is higher than the mean value $(I_{max}+I_{min})/2$, the area under the curve, the slope of the wash in, the area under the wash in and the area under the wash out are parameters suitable for tumoral vascularization or tumoral angiogenesis detection;
(ii) comparing said at least one parameter with a reference parameter.

11. A method according to claim 10, wherein said reference parameter is a parameter which is determined from a modeling performed, when resulting from the excitation of said contrast agent present in a reference substrate, according to a method that includes:
  acquiring a second input digital signal, which is a function of time t, in the form of two-dimensional data, said second input digital signal resulting from the excitation, within the reference substrate, of a substance adapted to emit a signal in response to said excitation;
  modeling said second input digital signal in function of a pre-established model;
  generating a second output digital signal made up from said modeling;
  and wherein said modeling is based on a model of the type:

$$a_0 + (a_1 - a_0) * \frac{A + \left(\frac{t}{a_2}\right)^p}{B + \left(\frac{t}{a_2}\right)^q}$$

where coefficients $a_0$, $a_1$, $a_2$, p, q, A and B are estimated on the basis of said two-dimensional data of the second input digital signal.

12. A method according to claim 11, wherein said reference substrate is chosen from the group consisting of:
  a substrate issued from a healthy subject; and
  said test substrate at a time t prior to injection of a therapeutic molecule into said test substrate.

13. A method according claim 10, further comprising, prior to step (i), injecting said contrast agent in said test substrate.

14. A method according to claim 10, comprising measuring an effect of therapeutic molecules in the test substrate.

15. A method according to claim 14, wherein the therapeutic molecules have an impact on tumoral microvascularization.

16. A method according to claim 15, the therapeutic molecules show antiangiogenic or antivascular properties.

17. A system for processing a digital signal comprising:
  means for acquiring an input digital signal F(t) as a function of time t in the form of two-dimensional data (t, F(t)) resulting from an excitation, within a test substrate, of a substance adapted to emit a signal in response to said excitation;
  means for modeling said input signal F(t) in function of a pre-established model;
  a generator configured to generate an output digital signal I(t) made up from said modeling;
  wherein said pre-established model is:

$$I(t) = a_0 + (a_1 - a_0) * \left(\frac{A + \left(\frac{t}{a_2}\right)^p}{B + \left(\frac{t}{a_2}\right)^q}\right)$$

wherein:
    the means for modeling and the generator are implemented using a computing device;
    $a_0$, $a_1$, $a_2$, p, q, A and B are coefficients to be estimated;
    said means for modeling comprises a solver configured to estimate said coefficients on the basis of said two-dimensional data;
    $a_1$ is a coefficient related to a value of a maximum of the output digital signal I(t);
    $a_0$ is a value of the output digital signal I(t);
    $a_2$ is a coefficient related to a time of the maximum of the output digital signal I(t);
    p is a coefficient related to an increase in the output digital signal I(t);
    q is a coefficient related to an decrease in the output digital signal I(t); and
    A and B are arbitrary parameters.

18. A system according to claim 17, wherein said acquiring means comprises an ultrasonic probe adapted to excite said substance.

19. A system according to claim 18, wherein said acquiring means is adapted to acquire a temporal digital signal $f_{xy}(t)$ in the form of four-dimensional data (t, x, y, $f_{xy}(t)$) resulting from said excitation, where $f_{xy}(t)$ is a physical unit that is measured at time t at a location indexed (x, y) in said test substrate, and said acquiring means further comprising means for transforming said four-dimensional data (t, x, y, $f_{xy}(t)$) into said two-dimensional data (t, F(t)), wherein said transforming includes computing the first input digital signal F(t) as a function of y and $f_{xy}(t)$.

20. An apparatus for tumoral vascularization detection in a test substrate, said apparatus comprising:
  a system for modeling an acquired signal in response to an excitation of a contrast agent in said substrate,
  means for determining at least one parameter from said modeling performed by said system,
  a comparator adapted to compare said at least one parameter with reference parameters,
  said system for modeling the acquired signal comprising:
  means for acquiring an input digital signal F(t) as a function of time t in the form of two-dimensional data (t, F(t)) resulting from the excitation, within a test substrate, of a substance adapted to emit a signal in response to said excitation;
  means for modeling said input signal F(t) in function of a pre-established model;
  a generator configured to generate an output digital signal I(t) made up from said modeling;
  said pre-established model being of the type of:

$$I(t) = a_0 + (a_1 - a_0) * \left(\frac{A + \left(\frac{t}{a_2}\right)^p}{B + \left(\frac{t}{a_2}\right)^q}\right)$$

wherein:
    the means for determining, comparator, means for modeling, and generator are implemented using a computing device;
    $a_0$, $a_1$, $a_2$, p, q, A and B are coefficients to be estimated,
    said means for modeling comprises a solver configured to estimate said coefficients on the basis of said two-dimensional data,
    said at least one parameter is chosen from the group comprising the maximal amplitude $PI = I_{max} - I_{mm}$ of said output signal I(t), where $I_{max}$ and $I_{min}$ are respectively the maximum and minimum values of I(t), the time for the output signal I(t) to reach its maximal amplitude PI from the beginning of the contrast uptake, the mean transit time corresponding to the time during which the value I(t) of the output signal is higher than the mean value $(I_{max}+I_{min})/2$,
    $a_1$ is a coefficient related to a value of a maximum of the output digital signal I(t),
    $a_0$ is a value of the output digital signal I(t), $a_2$ is a coefficient related to a time of the maximum of the output digital signal I(t), p is a coefficient related to an increase in the output digital signal I(t), q is a coefficient related to an decrease in the output digital signal I(t); and A and B are arbitrary parameters.

* * * * *